United States Patent [19]

Kober et al.

[11] Patent Number: 4,937,256
[45] Date of Patent: Jun. 26, 1990

[54] THIOPHENE COMPOUNDS

[75] Inventors: Reiner Kober, Fussgoenheim; Joachim Leyendecker, Ladenburg; Rainer Seele, Fussgoenheim; Stefan Karbach, Neustadt; Norbert Meyer, Landenburg; Karl-Otto Westphalen, Speyer; Bruno Wuerzer, Otterstadt; Gerhard Wagenblast, Frankenthal, all of Fed. Rep. of Germany

[73] Assignee: BASF Aktiengesellschaft, Ludwigshafen, Fed. Rep. of Germany

[21] Appl. No.: 356,552

[22] Filed: May 25, 1989

[30] Foreign Application Priority Data

Jun. 1, 1988 [DE] Fed. Rep. of Germany ....... 3818670

[51] Int. Cl.$^5$ .................... A01N 43/02; C07D 409/00
[52] U.S. Cl. ........................................ 514/444; 549/59
[58] Field of Search ........................... 549/59; 514/444

[56] References Cited

U.S. PATENT DOCUMENTS 3,050,442  8/1962  Bijloo et al. .

FOREIGN PATENT DOCUMENTS 2459666  7/1975  Fed. Rep. of Germany ........ 549/59

Primary Examiner—Alan Siegel
Attorney, Agent, or Firm—Oblon, Spivak, McClelland, Maier & Neustadt

[57] ABSTRACT

Thiophene compounds of the formula I

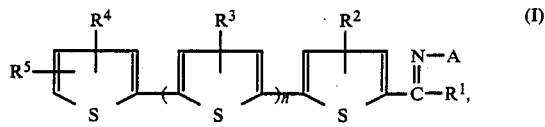

where the substituents and the index have the following meanings:

n is 0 or 1;

$R^1$ is hydrogen, halogen, $C_1$-$C_8$-alkyl, $C_1$-$C_6$-alkoxy, $C_1$-$C_8$-haloalkyl or $C_1$-$C_6$-haloalkoxy;

$R^2$, $R^3$, $R^4$ and $R^5$ are cyano, nitro or the groups given for $R^1$;

A is hydrogen, $C_1$-$C_8$-alkyl, $C_1$-$C_6$-haloalkyl, $C_1$-$C_8$-alkoxy, $C_1$-$C_6$-haloalkoxy, substituted or unsubstituted aryl or heteroaryl, a radical $OR^6$, where $R^6$ is hydrogen, $C_1$-$C_8$-alkyl, substituted $C_1$-$C_4$-alkyl, substituted or unsubstituted $C_2$-$C_8$-alkenyl, substituted or unsubstituted $C_3$-$C_7$-alkynyl, $C_4$-$C_9$-cycloalkyl, or a radical $NR^7R^8$, where $R^7$ and $R^8$ are hydrogen, $C_1$-$C_8$-alkyl, $C_1$-$C_8$-alkoxy, $C_1$-$C_6$-haloalkyl, $C_1$-$C_6$-haloalkoxy, substituted or unsubstituted aryl or hetaryl, substituted or unsubstituted $C_1$-$C_{12}$-alkylcarbonyl, $C_1$-$C_{12}$-haloalkylcarbonyl, substituted or unsubstituted aryl or hetaryl, and their environmentally acceptable salts, processes for their manufacture, and their use.

7 Claims, No Drawings

THIOPHENE COMPOUNDS

The present invention relates to thiophene compounds of the general formula I

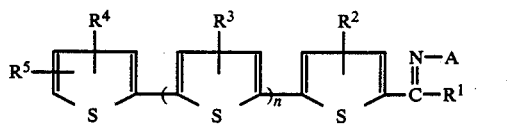

where n is 0 or 1;

$R^1$ is hydrogen, halogen, $C_1$–$C_8$-alkyl, $C_1$–$C_6$-alkoxy, $C_1$–$C_8$-haloalkyl or $C_1$–$C_6$-haloalkoxy;

$R^2$, $R^3$, $R^4$ and $R^5$ are each cyano, nitro or the groups stated for $R^1$;

A is hydrogen, $C_1$–$C_8$-alkyl, $C_1$–$C_6$-haloalkyl, $C_1$–$C_8$-alkoxy, $C_1$–$C_6$-haloalkoxy, aryl or hetaryl, and the aromatic groups may carry from one to five halogen atoms and/or from one to three of the following radicals: $C_1$–$C_8$-alkyl, $C_1$–$C_6$-haloalkyl, $C_1$–$C_8$-alkoxy, $C_1$–$C_6$-haloalkoxy, hydroxycarbonylamino and/or $C_1$–$C_4$-alkoxycarbonylamino; a radical $OR^6$, where $R^6$ is hydrogen, $C_1$–$C_8$-alkyl, $C_1$–$C_4$-alkyl which is monosubstituted to pentasubstituted by halogen and/or monosubstituted by one of the following radicals: cyano, $C_3$–$C_7$-cycloalkyl, hydroxyl, $C_1$–$C_4$-alkoxy, $C_1$–$C_4$-alkylcarbonyl-$C_1$–$C_4$-alkoxy, $C_3$–$C_7$-cycloalkylcarbonyl-$C_1$–$C_4$-alkoxy, $C_1$–$C_8$-alkylcarbonyl, $C_1$–$C_8$-haloalkylcarbonyl, $C_3$–$C_8$-cycloalkylcarbonyl, $C_1$–$C_8$-alkoxycarbonyl, mercapto, $C_1$–$C_4$-alkylthio, amino, $C_1$–$C_6$-alkylamino or di-$C_1$–$C_6$-alkylamino, where these alkyl groups together with the nitrogen atom may furthermore form an aliphatic ring, or is amino-$C_1$–$C_4$-alkoxy, $C_1$–$C_4$-alkylamino-$C_1$–$C_4$-alkoxy or di-$C_1$–$C_4$-alkylamino-$C_1$–$C_4$-alkoxy, where the alkyl groups together with the nitrogen atom may furthermore form an aliphatic ring, or five-membered or six-membered hetaryl containing from one to three of the heteroatoms nitrogen, oxygen and/or suflur, where this cyclic structure in turn may be monosubstituted to pentasubstituted by halogen and/or monosubstituted to trisubstituted by the following radicals:

$C_1$–$C_4$-alkyl, $C_1$–$C_4$-alkoxy, $C_1$–$C_4$-haloalkyl and/or $C_1$–$C_4$-haloalkoxy;

$C_3$–$C_9$-cycloalkyl;

$C_2$–$C_8$-alkenyl which may be monosubstituted to pentasubstituted by halogen and/or monosubstituted by $C_1$–$C_4$-alkoxy;

$C_3$–$C_7$-alkynyl which may be monosubstituted to pentasubstituted by halogen and/or monosubstituted by $C_1$–$C_4$-alkoxy;

or a radical $NR^7R^8$, where $R^7$ and $R^8$ are each hydrogen, $C_1$–$C_8$-alkyl, $C_1$–$C_8$-alkoxy, $C_1$–$C_6$-haloalkyl, $C_1$–$C_6$-haloalkoxy, aryl or hetaryl which may be monosubstituted to trisubstituted by halogen, $C_1$–$C_8$-alkyl, $C_1$–$C_8$-alkoxy, $C_1$–$C_6$-haloalkyl, $C_1$–$C_6$-haloalkoxy or alkoxycarbonylamino, or are each $C_1$–$C_{12}$-alkylcarbonyl, $C_1$–$C_{12}$-haloalkylcarbonyl, aroyl or hetaroyl which may be monosubstituted to trisubstituted by halogen, $C_1$–$C_5$-alkoxy, $C_1$–$C_4$-haloalkyl or $C_1$–$C_6$-alkyl, and their environmentally compatible salts.

The present invention furthermore relates to a process for the preparation of these compounds and their use in herbicides.

U.S. Pat. No. 3,050,442 describes bi- and terthienyl (bis- and terthiophene) compounds as agents for controlling nematodes. Some of these bi- and terthienyl compounds were found to have a herbicidal action, which, however, was unsatisfactory.

It is an object of the present invention to provide novel thiophene compounds having improved herbicidal properties.

We have found that this object is achieved by the thiophene compounds I defined at the outset. We have furthermore found a process for the preparation of the compounds I and their use for controlling undesirable plant growth.

The novel compounds I are obtained similarly to methods known from the literature, for example by reacting a corresponding thiophene compound of the formula II

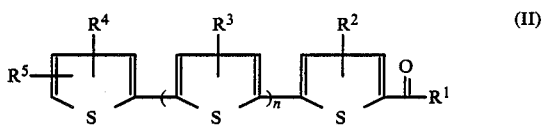

in a conventional manner with a corresponding hydroxylamino compound (or with the hydroxylammonium compound and a base) or with a correspondingly substituted hydrazine or with a correspondingly substituted primary amine.

Because of their biological activity, the substituents in the formula I preferably have the following meanings:

$R^1$ is hydrogen, halogen, such as fluorine, chlorine, bromine or iodine, preferably chlorine, alkyl, such as methyl, ethyl, propyl, 1-methylethyl, butyl, 1-methylpropyl, 2-methylpropyl or 1,1-dimethylethyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2-trifluoroethyl, 2-chloro-2,2-difluoroethyl, 2,2-dichloro-2-fluoroethyl, 2,2,2-trichloroethyl or pentafluoroethyl, or a corresponding haloalkoxy group, $R^2$, $R^3$, $R^4$ and $R^5$ are each cyano, nitro or the radicals stated in general and in particular for $R^1$, A is hydrogen, an alkyl, haloalkyl, alkoxy or haloalkoxy group as stated in general and in particular for $R^1$, aryl or hetaryl, such as phenyl, naphthyl, pyrrolyl, pyrazolyl, imidazolyl, isoxazolyl, oxazolyl, isothiazolyl, thiazolyl, furanyl, thienyl, pyridyl, pyridazinyl, pyrimidinyl, pyrazinyl, indolyl, isoindolyl, quinolyl, isoquinolyl or purinyl, in particular phenyl, furyl, pyridyl or thienyl, where these aromatic groups may carry from one to five of the halogen atoms stated under $R^1$, in particular fluorine, chlorine and/or bromine, and/or from one to three of the following radicals: alkyl, haloalkyl, alkoxy and haloalkoxy as stated for $R^1$, in particular methyl, 1-methylethyl, difluoromethyl, trifluoromethyl, chloromethyl, methoxy, ethoxy, isopropoxy, difluoromethoxy or trifluoromethoxy, or alkoxycarbonylamino, such as methoxycarbonylamino, ethoxycarbonylamino, propoxycarbonylamino, 1-methylethoxycarbonylamino or 1,1-dimethylethoxycarbonylamino, a radical $OR^6$, where $R^6$ is hydrogen, alkyl as stated for $R^1$, in particular methyl, ethyl, propyl or isopropyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular propen-2-yl or buten-2-yl, haloalkenyl, in particular 3-chloropropen-2-yl, 3,3-dichloropropen-2-yl or 4,4-dichlorobuten-2-yl, primary, secondary or tertiary aliphatic cyclic or acyclic aminoalkyl or aminoalkoxyalkyl, in particular 2-methylaminoethyl, 2,2-dimethylaminoethyl, 3,3-dimethylaminopropyl, N-methylaziridylmethyl, 2-aminoethyl, 2-(2-aminoethoxy)-ethyl or 2-(methylamino)-propyl, alkoxyalkyl, in particular methoxyethyl or ethoxyethyl, alkoxyalkenyl, in particular 3-methoxy-2-propenyl, alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl, haloalkynyl, in particular 3-chloro-2-propynyl, and in particular 2-cyanoethyl, cyclopropylmethyl, 2-cyclopropoxyethyl, 2-(2-cyclopropoxyethoxy)-ethyl, methoxycarbonylmethyl, 2-ethoxycarbonylethyl, N-methylaminocarbonylmethyl, (2,2-dimethylhydrazino)-carbonylmethyl, phenacyl, 3-chloro-2-oxobutyl, 2-methylthioethyl, 2-ethylthio-1-methylethyl or 3-mercaptopropyl, or a radical $NR^7R^8$, where $R^7$ and $R^8$ are each preferably phenyl, 4-chlorophenyl, 4-chloro-2-methylphenyl, furyl, 3-methoxycarbonylaminophenyl, 3-methoxyphenyl, 4-trifluoromethylphenyl, 4-(2-chloroethoxy)-phenyl, 2-pyridyl, 3-pyridyl, 2-thienyl, chloroacetyl, acetyl, benzoyl, 2-thienoyl, 2-pyridylcarbonyl, 3-chlorobenzoyl, 3-dimethylamino-2-methylbenzoyl, 3-methoxybenzoyl, 4-trifluoromethylbenzoyl or 5-methylfuroyl, and furthermore hydrogen and/or the alkyl, alkoxy, haloalkyl and haloalkoxy groups stated in general and in particular for $R^1$.

The novel thiophene compounds I, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butano, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably 95 to 100, % (NMR spectrum).

The compounds I according to the invention may be formulated for instance as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.028 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.049 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2.001 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2.002 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3.001 is intimately mixed with 97 parts by weight of particulate kaolin. A dust is obtained containing 3% by weight of the active ingredient.

VII. 30 parts by weight of compound no. 1.005 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.034 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or herbicidal agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beet, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |

| Botanical name | Common name |
| --- | --- |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, maize |

To increase the spectrum of action and to achieve synergistic effects, the novel thiophene compounds I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, aryloxy- or heteroaryloxyphenoxypropionic acids and salts, esters and amides thereof, etc.

It may also be useful to apply the compounds I, either alone or in combination with other herbicides, in admixture with other crop protection agents, e.g., agents for combating pests or phytopathogenic fungi or bacteria.

The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were employed, after appropriate modifications to the starting materials, to obtain further compounds of the formula I; the compounds obtained are listed in the tables below with physical data. Those compounds for which no data are given may be produced analogously from the appropriate materials. In view of their close structural similarity with the compounds produced and investigated, they are expected to have a similar action.

EXAMPLE 1

5'-Chloro-O-(2-butynyl)-2,2'-bithiophene-5-carbaldoxime

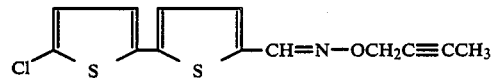

2.0 g of O-(2-butynyl)-hydroxylammonium oxalate is added to a mixture of 2.0 g of 5'-chloro-2,2'-bithiophene-5-carbaldehyde and 2.9 g of potassium acetate in 30 ml of 50% strength glacial acetic acid and 20 ml of isopropanol. The mixture is stirred for 6 hours at 60° C., and allowed to cool. Suction filtration and drying gives 3.3 g of crystals of melting point 104°–107° C., which, according to proton resonance spectroscopy, is an E/Z mixture in a ratio of 3:1.

EXAMPLE 2

O-Ethyl-2,2':5',2''-terthiophene-5-carbaldoxime

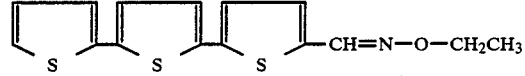

In accordance with Example 1, 2.2 g of sodium bicarbonate and 2.44 g of ethoxyammonium chloride are added to 6.9 g of 2,2':5',2''-terthiophene-5-carbaldehyde obtained according to the instructions given in Heterocyclces 24 (No. 3), 637–640 (1986) in 25 ml of methanol and 25 ml of methylene chloride. The mixture is stirred at room temperature for 10 hours and then concentrated; the residue is taken up in ethyl acetate. The mixture is washed with water and saturated bicarbonate solution, dried and concentrated under reduced pressure. The residue is recrystallized from hexane. there is obtained 4.1 g of a brown of melting point 49°–51° C.

TABLE 1.1

| No. | n | R⁵ | R⁴ | R¹ | R⁶ | Phys. data mp (°C.) |
| --- | --- | --- | --- | --- | --- | --- |
| 1.001 | 1 | H | H | H | —CH₂CH₃ | 49–51 |
| 1.002 | 1 | H | H | H | —CH₂CH=CH₂ | 54–56 |
| 1.003 | 1 | H | H | H | —CH₂CH=CHCl (trans) | 53–54 |
| 1.004 | 1 | H | H | H | —CH₂CH=CHCH₃ | 50–53 |

TABLE 1.1-continued

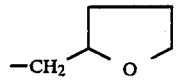

| No. | n | R⁵ | R⁴ | R¹ | R⁶ | Phys. data mp (°C.) |
|---|---|---|---|---|---|---|
| 1.005 | 1 | H | H | H | —CH(CH₃)C≡CH (trans) | 64–66 |
| 1.006 | 1 | H | H | CH₃ | —CH₂CH₃ | 61–66 |
| 1.007 | 1 | CH₃ | H | H | —CH₂CH₃ | |
| 1.008 | 1 | Br | H | H | CH₃ | |
| 1.009 | 1 | Cl | H | CH₃ | CH₃ | |
| 1.010 | 1 | H | H | H | —CH₂CH₂OCH₃ | |
| 1.011 | 1 | H | H | H | —CH₂CH₂N(CH₃)₂ | |
| 1.012 | 1 | H | H | H | —CH₂CN | |
| 1.013 | 1 | H | H | H | —CH₂CH(OCH₂CH₃)₂ | |
| 1.014 | 1 | H | H | H | —CH₂CH₂OCH₃ | |
| 1.015 | 1 | H | H | H | —CH₂CONH₂ | |
| 1.016 | 1 | H | H | H | —CH₂C≡CH | |
| 1.017 | 1 | H | H | H | —CH(CH₃)CH₂OCH₃ | |
| 1.018 | 1 | H | H | H | —CH₂CH₂Br | |
| 1.019 | 1 | Cl | H | H | —(CH₂)₂CH₂ | |
| 1.020 | 0 | H | H | H | —CH₂CH=CH₂ | oil |
| 1.021 | 0 | Cl | H | H | —CH₂CCl=CH₂ | 53–56 |
| 1.022 | 0 | Cl | H | H | —CH₂CH=CH₂ | resin |
| 1.023 | 0 | H | H | H | —CH₂CCl=CH₂ | |
| 1.024 | 0 | H | H | CH₃ | —CH₂CH=CH₂ | resin |
| 1.025 | 0 | H | H | CH₂CH₃ | —CH₂CH₃ | oil |
| 1.026 | 0 | H | H | CH₃ | —CH₂CH₃ | oil |
| 1.027 | 0 | H | H | CH₂CH₃ | —CH₂CH=CH₂ | oil |
| 1.028 | 0 | Cl | H | H | —CH₂CH=CHCl (cis) | 30–32 |
| 1.029 | 0 | Cl | H | H | —CH₂CH₃ | 55–58 |
| 1.030 | 0 | Cl | H | H | —CH₂CH=CHCl (trans) | 77–81 |
| 1.031 | 0 | Cl | H | H | —(CH₂)₂CH₃ | oil |
| 1.032 | 0 | Cl | H | H | —CH(CH₃)C≡CH | 72–75 |
| 1.033 | 0 | Cl | H | H | —CH₂—C≡CCH₃ | 104–107 |
| 1.034 | 0 | Cl | H | H | —CH₂—C≡CH | 88–92 |
| 1.035 | 0 | Cl | H | H | —CH₂CH₂N(CH₃)₂ | oil |
| 1.036 | 0 | Cl | H | H | —CH₂CHCl=CH₂ | 63–66 |
| 1.037 | 0 | Cl | H | H | —CH₂— (tetrahydrofuran-2-yl) | oil |
| 1.038 | 0 | Cl | H | H | —CH₃ | 92–94 |
| 1.039 | 0 | CH₃ | H | H | —CH₂C≡CH | oil |
| 1.040 | 0 | CH₃ | H | H | —CH₂CH=CH₂ | oil |
| 1.041 | 0 | CH₃ | H | H | —CH₂CH₃ | oil |
| 1.042 | 0 | I | H | H | —CH₂CH=CH₂ | oil |
| 1.043 | 0 | CH₃ | H | H | —CH₂CH₂N(CH₃)₂ | |
| 1.044 | 0 | CH₂CH₃ | H | H | —CH₂CH₂N(CH₃)₂ | |
| 1.045 | 0 | CH₂CH₃ | CH₂CH₃ | H | —CH₂CH₂OCH₃ | |
| 1.046 | 0 | Cl | Cl | H | —CH₂CH₂OCH₃ | |
| 1.047 | 0 | Cl | Cl | H | —CH₂CH₂CH₂N(CH₃)₂ | |
| 1.048 | 0 | CH₃ | CH₃ | H | —CH₂C≡N | |
| 1.049 | 0 | Cl | H | H | —CH₂CH₂Br | 70–73 |
| 1.050 | 0 | Cl | H | H | —CH₂CH₂Cl | |
| 1.051 | 0 | Cl | H | H | —CH₂CH₂OH | |
| 1.052 | 0 | CH₃ | H | H | —CH₂COOCH₂CH₃ | |
| 1.053 | 0 | CH₃ | H | H | —CH₂CONH₂ | |
| 1.054 | 0 | Cl | H | H | —CH₂CONHN(CH₃)₂ | |
| 1.055 | 0 | Cl | H | H | —CH₂COOCH₃ | |
| 1.056 | 0 | Cl | H | H | —CH₂CH₂N(CH₃)₂ | |
| 1.057 | 0 | Cl | H | H | —CH₂CH₂OCH₂CH₃ | |
| 1.058 | 0 | H | H | H | —CH₂CH₂N(CH₃)₂ | |
| 1.059 | 0 | Cl | H | H | —CH₂CH₂N(CH₃)₂ | |
| 1.060 | 0 | CH₂CH₃ | H | H | —CH₂CH₂NH₂ | |
| 1.061 | 0 | Cl | H | H | —CH₂CH₂NHCH₂CH₃ | |
| 1.062 | 0 | Cl | H | H | —CH₂CH₂NHCHO | |
| 1.063 | 0 | Cl | Cl | H | —CH₂CH=CH₂ | |
| 1.064 | CH₃ | CH₃ | H | H | —CH₂CH₂COOH | |
| 1.065 | 0 | CH₂CH₃ | H | H | —CH₂CH₂NHCH₃ | |
| 1.066 | 0 | Cl | Cl | H | —CH₂CH₂OCH₃ | |
| 1.067 | 0 | Cl | Cl | CH₃ | —CH₂CH₂NHCH₃ | |
| 1.068 | 0 | Cl | H | H | —CH₂CH₂SH | |
| 1.069 | 0 | Cl | H | H | —CH₂CH₂SCH₃ | |
| 1.070 | 0 | Cl | H | H | —CH₂CH₂SCH₂CH₃ | |

TABLE 1.1-continued

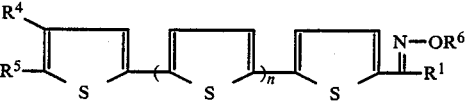

| No. | n | R⁵ | R⁴ | R¹ | R⁶ | Phys. data mp (°C.) |
|---|---|---|---|---|---|---|
| 1.071 | 0 | Cl | Cl | H | —CH₂CH₂S(CH₂)₂CH₃ | |
| 1.072 | 0 | Cl | H | H | —CH₂NHCOCH₃ | |
| 1.073 | 0 | Cl | H | H | —CH₂CH₂COCH₃ | |
| 1.074 | 0 | Cl | H | H | —CH₂CH₂COCH₂Cl | |
| 1.075 | 0 | Cl | H | H | —CH₂CH₂CH₂OCH₃ | |
| 1.076 | 0 | Cl | H | H | —CH₂CH₂O—△ | |
| 1.077 | 0 | Cl | H | H | —CH₂CH₂CH=CHCl | |

TABLE 1.2

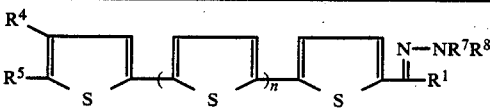

| No. | n | R⁵ | R⁴ | R¹ | R⁷ | R⁸ | Phys. data mp (°C.) |
|---|---|---|---|---|---|---|---|
| 2.001 | 1 | H | H | H | H | —CONH₂ | 220 |
| 2.002 | 1 | H | H | H | H | phenyl | 183–186 |
| 2.003 | 1 | H | H | H | H | 4-F-phenyl | |
| 2.004 | 1 | H | H | H | Me | —COCH₃ | |
| 2.005 | 1 | H | H | H | H | —COCH₃ | |
| 2.006 | 1 | H | H | H | Me | —COCH₂Cl | |
| 2.007 | 1 | H | H | H | H | —COOCH₂CH₃ | |
| 2.008 | 1 | H | H | H | H | —COCH₃ | |
| 2.009 | 1 | H | H | H | Me | —CHO | |
| 2.010 | 1 | H | H | H | Me | methyl | |
| 2.011 | 1 | H | H | H | Et | ethyl | |
| 2.012 | 0 | Cl | H | H | Et | ethyl | |
| 2.013 | 0 | Cl | Cl | H | Me | —CHOCH₂Cl | |
| 2.014 | 0 | Me | Me | H | H | —COCH₂N(CH₃)₂ | |
| 2.015 | 0 | Cl | H | H | H | —COCH₂N(CH₃)₂ | |

TABLE 1.3

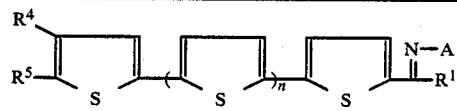

| No. | n | R⁵ | R⁴ | R¹ | A | Phys. data mp (°C.) |
|---|---|---|---|---|---|---|
| 3.001 | 1 | H | H | H | Ph | 157–159 |
| 3.002 | 1 | H | H | H | 4-Cl-phenyl | |
| 3.003 | 1 | H | H | H | 4-F-phenyl | |
| 3.004 | 1 | H | H | H | 4-CH₃-phenyl | |
| 3.005 | 1 | H | H | H | 2-pyridyl | |
| 3.006 | 1 | H | H | Me | 2-(5-methylpyridyl) | |
| 3.007 | 1 | H | H | H | 2-thienyl | |
| 3.008 | 1 | H | H | H | 5-(1,2,4-triazolyl) | |
| 3.009 | 1 | H | H | H | 5-(2-methyl-1,3-oxazolyl) or 2-methyl-1,3-oxazol-5-yl | |
| 3.010 | 1 | H | H | H | 5-(2-ethyl-1,3-oxazyl) | |
| 3.011 | 1 | H | H | H | 2-Cl-phenyl | |
| 3.012 | 0 | Cl | H | H | 5-(1,2,4-triazyl) | |
| 3.013 | 0 | H | H | H | 5-(1,2,4-triazyl) | 166–168 |
| 3.014 | 0 | Cl | H | Me | 5-(1,2,4-triazyl) | |

USE EXAMPLES

The action of the thiophene compounds of the formula I on plant growth is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rate for postemergence treatment was 0.25 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were as follows:

| Abbreviation | Botanical name | Common name |
|---|---|---|
| ABUTH | Abutilon theophrasti | velvet leaf |
| AMARE | Amaranthus retroflexus | redroot pigweed |
| CHEAL | Chenopodium album | lambsquarters |
| DATST | Datura stramonium | jimsonweed |
| LAMAM | Lamium amplexicaule | dead-nettle |
| ORYSA | Oryza sativa | rice |
| SOLNI | Solanum nigrum | black nightshade |
| STEME | Stellaria media | chickweed |
| VERSS | Veronica spp. | speedwell |

Compounds 1.001, 1.002 and 1.035, applied postemergence at a rate of 0.25 kg/ha, had an excellent action on unwanted plants. Rice suffered only slight damage, if at all.

Compound 1.001, applied postemergence at a rate of 0.25 kg/ha, had a herbicidal action on *Abutilon theophrasti, Datura stramonium* and *Lamium amplexicaule*.

We claim:

1. A thiophene compound of formula I:

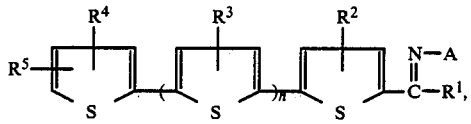

where the substituents and the index have the following meanings:

n is 0 or 1;

$R^1$ is hydrogen, halogen, $C_1$-$C_8$-alkyl, $C_1$-$C_6$-alkoxy, $C_1$-$C_8$-haloalkyl or $C_1$-$C_6$-haloalkoxy;

$R^2$, $R^3$, $R^4$ and $R^5$ are each cyano, nitro or the groups stated for $R^1$, with the proviso that $R^4$ and $R^5$ do not denote nitro when n=0 and $R^1$ is hydrogen;

A is hydrogen, $C_1$-$C_8$-alkyl, $C_1$-$C_6$-haloalkyl, $C_1$-$C_8$-alkoxy, $C_1$-$C_6$-haloalkoxy, phenyl or naphthyl, and environmentally acceptable salts thereof.

2. The thiophene compound of claim 1, wherein, for said substituent $R^1$, halogen is fluorine, chlorine, bromine or iodine; alkyl is methyl, ethyl, propyl, 1-methylethyl, butyl, 1-methylpropyl, 2-methylpropyl or 1,1-dimethylethyl; alkoxy is methoxy, ethoxy, propoxy, 1-methylethoxy, butoxy, 1-methylpropoxy, 2-methylpropoxy or 1,1-dimethylethoxy; haloalkyl is fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2-trifluoroethyl, 2-chloro-2,2-difluoroethyl, 2,2-dichloro-2-fluoroethyl, 2,2,2-trichloroethyl or pentafluoroethyl; and said haloalkoxy radicals are the corresponding oxy radicals of the haloalkyl radicals.

3. The thiophene compound of claim 1, wherein, for substituent A, hydrogen, $C_1$-$C_8$-alkyl, $C_1$-$C_6$-haloalkyl, $C_1$-$C_8$-alkoxy and $C_1$-$C_6$-haloalkoxy are the radicals specified in claim 2.

4. A herbicidal agent containing a thiophene derivative of the formula I as set forth in claim 1, and inert additives.

5. A process for combating the growth of unwanted plants, wherein the unwanted plants and/or their habitat are treated with a herbicidally effective amount of a thiophene derivative I as set forth in claim 1.

6. The process of claim 5, wherein the amount of said thiophene derivative is applied over the range of from 0.001 to 5.0 kg per hectare.

7. The herbicidal agent of claim 4, wherein said formulation contains from 0.1 to 95% by weight of said thiophene derivative.

* * * * *